US00PP10889P

United States Patent [19]

Clucas

[11] Patent Number: Plant 10,889

[45] Date of Patent: May 11, 1999

[54] BRACHYCOME PLANT NAME 'BILLABONG MAUVE DELIGHT'

[75] Inventor: Evan Philip Clucas, Wandin North, Australia

[73] Assignee: Outback Plants Pty. Ltd., Victoria, Australia

[21] Appl. No.: 08/938,581

[22] Filed: Sep. 26, 1997

[51] Int. Cl.[6] ..... A01H 5/00

[52] U.S. Cl. ..... Plt./68.1

[58] Field of Search ..... Plt./68.1

*Primary Examiner*—Howard J. Locker
*Assistant Examiner*—Melissa L. Kimball
*Attorney, Agent, or Firm*—C. A. Whealy

[57] ABSTRACT

A new and distinct cultivar of *Brachycome angustifolia* named 'Billabong Mauve Delight', characterized by its compact, low-growing, flat and spreading plant habit; fast production time; freely branching plant habit; numerous inflorescences with light purple ray florets and yellow green disc florets; and erect peduncles that hold inflorescences above the foliage.

1 Drawing Sheet

The present invention relates to a new and distinct cultivar of Brachycome plant, botanically known as *Brachycome angustifolia* and referred to by the cultivar name Billabong Mauve Delight.

The new cultivar was discovered by the inventor in a group of seedling progeny from a cross of unidentified selections of *Brachycome angustifolia* in an outdoor area in Wandin North, Victoria, Australia.

Asexual reproduction of the new cultivar by terminal cuttings taken in a controlled environment in Wandin North, Victoria, Australia, has shown that the unique features of this new Brachycome are stable and are reproduced true to type in successive generations.

The new cultivar has not been observed under all possible environmental conditions. The phenotype may vary somewhat with variations such as temperature, daylength and light intensity, without, however, any variance in genotype.

The following characteristics have been repeatedly observed and are determined to be basic characteristics of 'Billabong Mauve Delight' and distinguish 'Billabong Mauve Delight' as a new and distinct cultivar:

1. Compact, low-growing, flat and spreading plant habit.
2. Fast production time.
3. Freely branching plant habit. Plants do not require pinching.
4. Numerous inflorescences with light purple ray florets and yellow green disc florets.
5. Erect peduncles that hold inflorescences above the foliage.

The new Brachycome can be compared to the nonpatented *Brachycome angustifolia* cultivar Mauve Flower Form. Compared to plants of the cultivar Mauve Flower Form, plants of the new Brachycome are more compact, more floriferous, and have darker ray floret color. Additionally leaves of plants of the new Brachycome are 3 to 5-lobed, whereas leaves of plants of the cultivar Mauve Flower Form are usually entire or occasionally with 1 or 2 lobes.

BRIEF DESCRIPTION OF THE PHOTOGRAPH

The accompanying colored photograph illustrates the overall appearance of the new cultivar, showing the colors as true as it is reasonably possible to obtain in colored reproductions of this type.

The photograph comprises a top perspective view of a single potted plant of 'Billabong Mauve Delight'. Floret and foliage colors in the photographs may appear different from the actual colors due to light reflectance.

DETAILED BOTANICAL DESCRIPTION

The following observations, measurements, values, and comparisons describe plants grown in Wandin North, Victoria, Australia, under outdoor conditions with day temperatures ranging from 15 to 40° C., night temperatures ranging from 8 to 25° C., and light levels ranging from 5,000 to 9,000 footcandles. Color references are made to The Royal Horticultural Society Colour Chart except where general terms of ordinary dictionary significance are used.

Classification:

*Botanical.*—*Brachycome angustifolia* cultivar Billabong Mauve Delight.

*Commercial.*—Brachycome.

Parentage:

*Male or pollen parent.*—Unidentified selection of *Brachycome angustifolia.*

*Female or seed parent.*—Unidentified selection of *Brachycome angustifolia.*

Propagation:

*Type.*—By cuttings.

*Time to initiate and develop roots.*—Summer: 10 to 20 days at temperatures of 25° C. Winter: 15 to 30 days at temperatures of 20° C.

*Rooting habit.*—Fine, fibrous and freely branching.

Plant description:

*General appearance.*—Compact, low-growing, flat and spreading, herbaceous plant with erect peduncles. Appropriate for hanging baskets and 10.5 to 15-cm containers. To produce a 15-cm finished flowering plant from rooted cuttings, 8 to 12 weeks are required depending on temperature and light level.

*Plant height.*—10 to 20 cm from soil level to top of inflorescences.

*Plant diameter or spread.*—30 to 60 cm.

*Branching.*—Freely branching, numerous lateral branches develop without removing the terminal apex (pinched).

*Growth rate/vigor.*—Moderate.

*Stem description.*—Lateral branch length: 2 to 6.5 cm. Lateral branch diameter: About 1 mm. Internode length: 0.7 to 1.5 cm. Texture: Glabrous. Color: 137D.

*Foliage description.*—Arrangement: Alternate, single. Quantity: 5 to 12 per lateral branch. Shape: Oblong with 3 to 5 lobes. Apex: Acute to somewhat obtuse.

Base: Sessile, attenuate. Length: 1 to 3.5 cm. Width: 0.5 to 1.5 cm. Texture: Smooth, glabrous, thin. Color: Young leaves, upper surface: 137A. Young leaves, lower surface: 137C. Fully expanded leaves, upper surface: 137B. Fully expanded leaves, lower surface: 138B. Venation: Same as leaf surfaces.

Flowering description:

*Infloresscence.*—Single daisy-type composite inflorescence form. Florets arranged acropetally on a capitulum. Inflorescences last on the plant for 2 to 3 weeks and 5 to 7 days as a fresh cut flower. Inflorescences semi-persistent.

*Natural flowering season.*—Natural flowering season is spring to fall. Plants flower continuously during this period.

*Quantity of inflorescences per lateral branch.*—One.

*Quantity of buds per lateral branch.*—One to three.

*Inflorescence diameter.*—1.5 to 2 cm.

*Inflorescence depth (height).*—4 to 8 mm.

*Inflorescence aspect.*—Flat.

*Fragrance.*—Negligible.

*Ray florets.*—Quantity: 16 to 25 florets per inflorescence arranged in one to two rows. Shape: Oblong to linear. Apex: Cordate or notched. Base: Attenuate. Margin: Entire. Aspect: Flat. Length: 6 to 10 mm. Width: About 2 mm. Texture: Smooth, glabrous, thin. Color: When opening, upper surface: 87B. When opening, lower surface: 84C. Mature, upper surface: 88C, with further development, floret color fades to 85A. Mature, lower surface: 84C.

*Disc florets.*—Shape: Tubular with five lobes. Diameter of disc: About 1 mm. Disc floret length: About 3 mm. Disc floret width: About 1 mm. Color: Immature: 154B. Mature: 154C. Number of disc florets per inflorescence: Numerous.

*Peduncle.*—Length: 4.2 to 5.5 cm. Strength: Moderately strong, inflorescences held erect above foliage. Texture: Smooth, glabrous. Color: 138C.

*Flower bud.*—Rate of opening: 5 to 7 days. Shape: Depressed spherical. Length: 1 to 2 mm. Diameter: 2 to 3 mm. Color: 138A.

*Involucral bracts.*—Arrangement: Imbricate. Quantity: 14 to 18 per inflorescence. Shape: Oblong, keeled, concave. Apex: Pointed to blunt, ciliate. Margin: Entire and ciliate. Color: 138C.

*Androecium.*—Only present on disc florets. Stamen number: Five per disc floret. Anther shape: Oblong to linear. Anther color: 22C. Amount of pollen: Moderate. Pollen color: 158A.

*Gynoecium.*—Pistil number: One per floret. Stigma shape: Bilobate. Style length: About 2 mm. Style color: 154A. Stigma color: 154C.

Disease resistance: May be susceptible to Botrytis in poorly ventilated areas.

Seed production: Seed production is typically not observed.

It is claimed:

1. A new and distinct cultivar of *Brachycome angustifolia* named 'Billabong Mauve Delight', as illustrated and described.

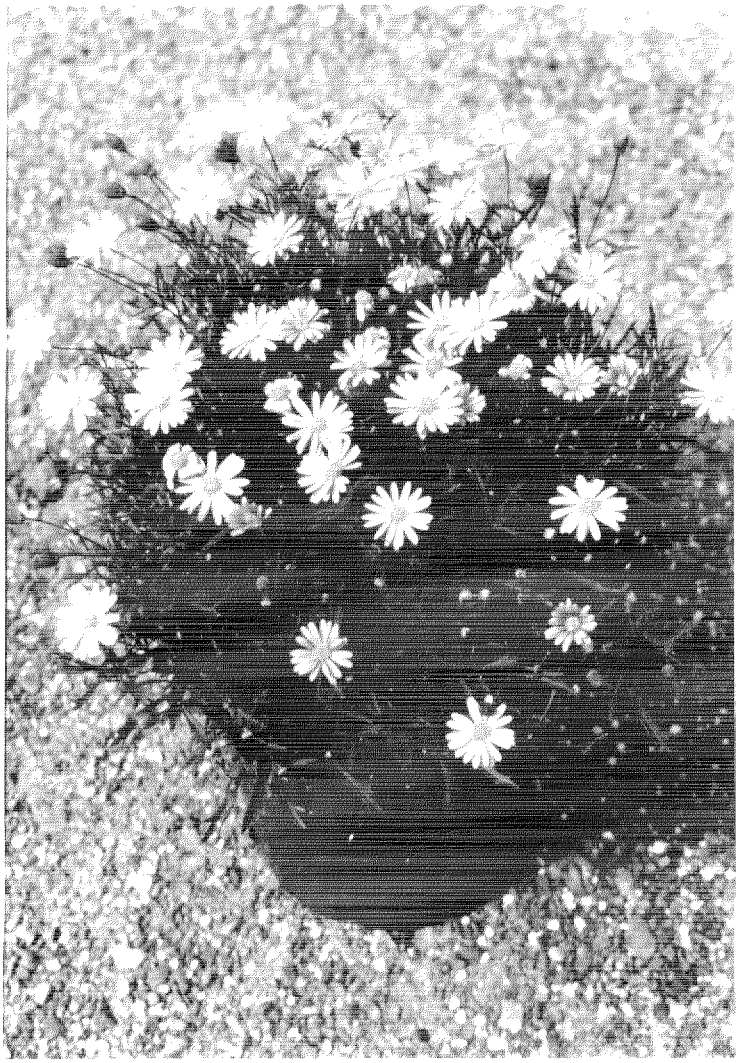

* * * * *